(12) United States Patent
Crosby et al.

(10) Patent No.: US 8,321,139 B2
(45) Date of Patent: Nov. 27, 2012

(54) METHODS AND APPARATUS FOR MODULUS MEASUREMENT

(75) Inventors: Alfred J. Crosby, Amherst, MA (US); Jessica Zimberlin, Amherst, MA (US)

(73) Assignee: University of Massachusetts, Boston, MA (US)

(*) Notice: Subject to any disclaimer, the term of this patent is extended or adjusted under 35 U.S.C. 154(b) by 1594 days.

(21) Appl. No.: 11/724,645

(22) Filed: Mar. 15, 2007

(65) Prior Publication Data
US 2010/0286555 A1    Nov. 11, 2010

Related U.S. Application Data

(60) Provisional application No. 60/782,418, filed on Mar. 15, 2006.

(51) Int. Cl.
*A61B 10/00* (2006.01)
(52) U.S. Cl. .......................... 702/19; 600/562
(58) Field of Classification Search ................ 702/1, 19, 702/33, 47; 600/557, 561, 587, 562
See application file for complete search history.

(56) References Cited

OTHER PUBLICATIONS

Zimberlin et al. "Cavitation Rheology for Soft Materials," Soft MAtter, 2007, 3, pp. 763-767. Nov. 22, 2006.*
Plesset, MS; Prosperetti, A. Bubble Dynamics and Cavitation. Am. Rev. Fluid Mech., 1977, pp. 145-185.
Koval'chuk, VL; Fainerman, VB; Miller, R; Dukhin, SS. Bubble formation in maximum bubble pressure measuring systems employing a gas reservoir of limited volume. Colloids and Surfaces A: Physiochem. and Eng. Aspects 143 (1998) pp. 381-393.
Bubble Pressure Analyser BPA-1P. Sinterface Technologies 2003. pp. 1-16.
Fainerman, VB; Miller, R; Joos, P. The measurement of dynamic surface tension by the maximum bubble pressure method. Colloid Polym. Sci. 272:272-739 (1994).
Zimberlin, JA; Sanabria-DeLong, N; Tew, GN; Crosby, AJ. Cavitation rheology for soft materials. Soft Matter, 2007, 3, pp. 763-767.

* cited by examiner

*Primary Examiner* — Sujoy Kundu
(74) *Attorney, Agent, or Firm* — Cantor Colburn LLP (57) ABSTRACT

Methods and system/apparatus as can be used to determine a material mechanical modulus on length scales as can be of biological cell dimension.

26 Claims, 5 Drawing Sheets

METHODS AND APPARATUS FOR MODULUS MEASUREMENT

This application claims priority benefit from application Ser. No. 60/782,418 filed on Mar. 15, 2006, the entirety of which is incorporated herein by reference.

BACKGROUND OF THE INVENTION

In the field of tissue engineering, research has determined that the mechanical properties of a substrate to which cells attach mediate different aspects of cell function including attachment, proliferation, migration, and differentiation. As these effects can be very pronounced, it is imperative to determine the stiffness of soft materials used in tissue engineering. Numerous techniques are available for measuring the mechanical modulus of a material, each with distinct advantages and disadvantages for the field of tissue engineering.

For instance, shear rheometry can be used on macroscopic length scales for measurement of elastic and/or viscoelastic measurements. Gel points can be readily determined, and the technique provides an "average" response. However, material heterogeneities cannot be probed. Further, shear rheometry requires a relatively large amount of material, often not available or practical. Equipment set-up is expensive and requires considerable training.

Contact mechanical tests are, likewise, often employed for modulus measurements on length scales of cellular (i.e., mesoscopic) dimensions. However, as such techniques probe only surface properties, the resulting data is not representative of the bulk material. Again, equipment is expensive and requires considerable training.

Techniques such as microbead rheology can be used to probe microscopic length scales, and modulus measurements produce values similar to traditional rheology. However, such techniques are generally restricted to softer (<100 Pa) materials and the microbeads can disturb natural gel formation. Again, such techniques typically require training and expertise of the sort precluding routine laboratory applications.

All of the aforementioned techniques are complicated, require an undue amount of training, and can be extremely expensive. As a result, the search for an effective, cost-efficient method for material analysis remains an on-going concern in the art. One such approach involves cavitation and subsequent measurement of mechanical moduli. However, previous such techniques and related apparatus have been limited to surface energy analysis of liquids.

SUMMARY OF THE INVENTION

In light of the foregoing, it is an object of the present invention to provide an apparatus and/or method(s) for material modulus measurement, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide an inexpensive, effective apparatus for the quick and efficient measurement of material moduli, such moduli as can be localized and varied over, across and/or throughout such a material.

It can be another object of the present invention to provide a cavitation method, system and/or apparatus useful in conjunction therewith for modulus measurements of a non-liquid material.

It can be another object of this invention, alone or in conjunction with one or more of the preceding objectives, to use such a method and/or apparatus to develop a useful biological or biomimetic tissue scaffold.

Other objects, features, benefits and advantages of the present invention will be apparent from this summary and the following descriptions of certain embodiments, and will be readily apparent to those skilled in the art having knowledge of various mechanical measurement and analytic techniques. Such objects, features, benefits and advantages will be apparent from the above as taken into conjunction with the accompanying examples, data, figures and all reasonable inferences to be drawn therefrom, alone or with consideration of the references incorporated herein.

In part, the present invention can comprise a method of determining a mechanical modulus of a material. Such a method can comprise providing a material or material substrate; applying a fluid to the material for at least one of a time and at a rate sufficient to induce or form a void or cavity within the material; sensing and/or monitoring the pressure within the void; and determining a mechanical modulus of the material. As would be understood by those skilled in the art, using known mathematical and physical relationships, various mechanical moduli can be determined by monitoring pressure or change thereof. In certain embodiments, such moduli can include but are not limited to the shear and elastic moduli of a particular material.

Regardless of any one or more moduli, such a method can be used in conjunction with various non-liquid materials. Representative materials include but are not limited to gels and related gelation systems (e.g., without limitation, elastomers, swollen elastomers, swollen networks and the like where the swelling agent can be aqueous or organic and the network can be natural or synthetic). Accordingly, materials useful with such an invention can include a range of hydrogels. Certain embodiments of this invention can be illustrated through analyses of polyvinyl alcohol (PVA) hydrogels over a range of PVA concentrations. Likewise, demonstrating various other embodiments of this invention, collagen gels and other biomimetic materials can be used herewith to simulate analysis of biological tissues. In certain other embodiments, biological tissues including but not limited to small intestinal submucosa (SIS), comprising one or more collagen components, can be used as described more fully below, to assess or determine one or more mechanical moduli thereof.

The fluid applied to such a material can comprise a liquid, a gas, air or a mixture thereof, can optionally be substantially immiscible with such a material, and can be introduced at a rate and/or for a time sufficient to induce or form a void or cavity within the material. In certain embodiments, such a void can be induced or formed so as to determine one or more moduli with respect to a material locale. In certain other embodiments, such a method can comprise a plurality of voids or cavities along, across or throughout the material, as can be used to assess any structural and/or compositional heterogeneity associated with such a material.

Accordingly, this invention can also be directed to a method of using cavitation to determine an elastic modulus or another mechanical modulus or variation thereof along, over or though a material. Such a method can comprise providing a material; applying a fluid to the material for at least one of a time and at a rate sufficient to induce or form a cavity within the material; sensing and/or monitoring the pressure within the cavity; and determining an elastic modulus or other mechanical modulus of the material. A plurality of such determinations over or throughout a material can be used to assess changes or variations in one or more such moduli therein, with optional correlation of material structure or composition associated therewith. In certain embodiments, as would be useful for various end-use applications, such determinations can be made over micron length scales.

Regardless of method or parameter measured, this invention can also be, in part, directed to an apparatus or system for measurement or assessment of one or more mechanical moduli. Such a system can comprise a material selected from a biological tissue and a biomimetic material; and a fluid source in fluid communication with a material contact component and a pressure sensor component. The sensor component can be interfaced with a suitable monitoring or recordation component to assess and/or monitor pressure as a function of time, and relate such pressure and/or change thereof to one or more mechanical moduli. In certain such embodiments, such a monitor can comprise a computer component interfaced with a sensor component. In certain embodiments, such an apparatus can comprise a camera or video image component to record cavity inducement, formation and/or change upon fluid contact with a material under analysis.

DETAILED DESCRIPTIONS OF THE DRAWINGS

DETAILED DESCRIPTION OF CERTAIN EMBODIMENTS

The present invention provides a ready method by which to determine a modulus on length scales similar to biological cells (~10-~50 µm) at specific points within a material. As illustrated by several representative embodiments, such a method can involve inducing a single cavity within a soft gel material and quantifying a critical pressure of mechanical instability. The pressure of the instability is directly related to the modulus of the material. As this method measures the modulus local to the site of cavitation, heterogeneities within a material can easily be probed. This capability is particularly important for monitoring the heterogeneities within a scaffold structure or local mechanical property changes within a native structure. Illustrating certain embodiments of this invention, consider that the composition and physical properties of SIS vary critically at cellular length scales, and that these variations are crucial to the function of this material. Characterization of these properties will enable the development of functional equivalents for tissue engineering applications.

A fundamental concept in materials science is that of the structure-property relationship. Correlating the composition and microstructure to the properties provides a deep level of understanding of materials and is the foundation for designing materials for specialized applications. While biological materials such as SIS have significantly more complicated compositions and structures and a broader range of properties that must be considered, this basic concept can still form the basis for materials development.

It is hypothesized that SIS properties are attributed to three factors: the organization of extracellular matrix (ECM) components, the micromechanical properties, and the interactions of the matrix with growth factors and cytokines. In native tissues, these three properties vary critically at cellular length scales, and characterization tools must be developed and applied that are capable of measuring properties at these length scales.

Porcine SIS is prepared by removing the mucosa, outer mesenteric tissues, and smooth muscle layers from the small intestine, leaving a 100-150 µm thick, semi-transparent membrane. The remaining tissue is primarily collagen type I but also contains collagen types III and VI, laminin, glycosaminoglycans such as hyaluronic acid, chondroitin sulfate, and heparan sulfate, as well as adhesive glycoproteins such as fibronectin These non-collagenous ECM components are thought to play important roles in cell adhesion and interactions with growth factors while the collagen matrix largely determines the mechanical properties.

Measuring the local mechanical properties of soft tissues can be especially important with thin tissues and with tissues whose properties change by layer. For instance, to fully characterize the adhesive properties of such thin sheets, local mechanical properties must be fully understood. PVA has been used to model ECM, and can provide a system on which to extend the utility of this invention. For instance, both collagen and PVA provide networks with pore sizes on the micron length scale. Accordingly, as provided more fully below, results obtained through probing PVA matrices can be extended in a straight forward manner, as shown, to collagen materials and can be used to assess SIS systems and the development of functional equivalents for tissue engineering applications.

Without limitation to any one theory or mode of operation, this invention can be considered in relation to the resistance and stability of micro-cavities, or bubbles, in liquids. In these systems, the relationship between pressure and volume in the bubble and the stability of the cavity can be related to the viscosity, cohesive energy density, surface energy, and dynamic and environmental conditions. For soft polymer networks, such as elastomers, the growth of a micro-cavity, or bubble, is dictated by a non-linear relationship between pressure and local extension ratio. This non-linear relationship is centrally dictated by the elastic modulus, E, of the polymer network. As others have demonstrated for elastomers, the critical pressure for expanding a spherical cavity is closely related to the elastic modulus of the surrounding material, E. For materials that obey the simple kinetic theory of rubber elasticity, the relationship between the pressure (P), the local modulus (E), and the radius of a cavity (r), is given by:

$$P = \frac{E}{6}\left(5 - 4\left(\frac{r_o}{r}\right) - \left(\frac{r_o}{r}\right)^4\right) \quad (1)$$

Bubble growth can be considered as including two phases. First, a growth phase can be characterized by radius of curvature decreasing up to a hemisphere. In a second release phase, the radius of curvature starts to increase until the bubble is released. The pressure peaks at a transition between their growth and release phases, and can be designated as $P_{max}$.

The resistance of a material to the internal growth of a void comes from both elastic forces and surfaces tension forces. Although not conclusive, the relationship between the pressure, P, inside the void and its radius, i, is phenomenologically related to when the void is initially considered to be spherical in nature as opposed to being initially considered a flat penny shaped void:

$$P/G = \frac{5}{2} - 2\frac{r_o}{r} - \frac{1}{2}\left(\frac{r_o}{r}\right)^4 + \frac{2\gamma}{Gr} \quad (2)$$

where G is the shear modulus of the material (assumed to be neo-hookean), $r_o$ is the void radius before cavitation, and $\gamma$ is the surface energy. In experiments, the introduction of the needle introduces a 'small hole' equivalent to those studied in the art. Gent, A. N.; Tompkins, D. A. *Journal of Applied Physics* 1969, 40, (6), 2520-&. Gent, A. N.; Wang, C. *Journal of Materials Science* 1991, 26, (12), 3392-3395. As the pressure inside the void increases, it will pass a critical point, $P_c$, where the void will start to grow and the value of $r/r_o$ approaches infinity. It is at this point that equation 1 reduces to:

$$P_c = \frac{5}{2}G + \frac{2\gamma}{r} \quad (3)$$

where the first term represents the energy required to elastically deform the material and the second term represents the energy required to create new surface area.

At a critical pressure, the cavity transitions through an instability that is marked by a sudden decrease in pressure. The pressure of the instability is directly related to a modulus of the material. As the method measures a modulus local to the cavitation, materials whose mechanical properties change depending on location can easily be probed. This capability can be particularly important for monitoring heterogeneities within a scaffold structure or local mechanical changes within a native structure. For example, the present methods and/or apparatus can be used to probe biological tissues with integrated layered structures, such structures including but not limited to the mitral valve or the eye. As shown below, the process of gelation and mechanical response of these hydrogels can be monitored, assessed and evaluated on micron length scales.

Figure 3:
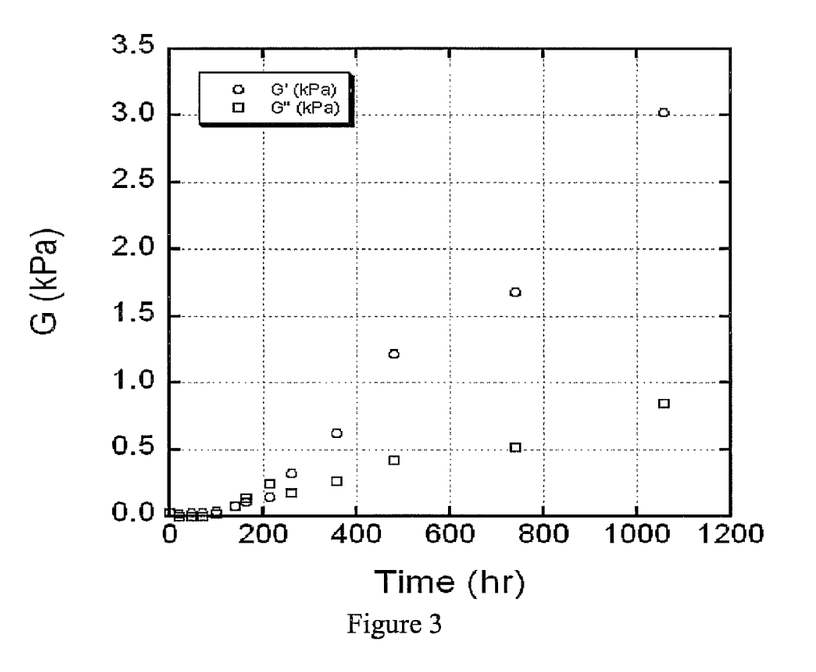
FIG. 3. Measurement of shear modulus over time for representative PVA gels.

The bulk properties of the PVA gels were first studied by cone and plate rheometry. A time sweep was run on the gels to monitor the change in the linear shear modulus, G', over time. (FIG. 3.) The graph shows an increase in G' with time and after about 200 hours a more pronounced increase in G'. This transition in slope corresponds to the gel point of the PVA as it was on the eighth day that the gel behaved solid like when the jar was tipped to the side.

The results here are consistent with literature experiments and the theory that after the PVA gel has passed its gel point, the hydrogel continues to become stiffer as it undergoes the process of syneresis. It is during syneresis that the gels will shrink in volume due to solvent exclusion, increase the amount of crystalline regions and therefore increase in mechanical strength. It is even seen that it is not until after 200 days that the gels finally reach an equilibrium state.

In developing an illustrative embodiment of this invention for measuring the shear modulus for PVA gels, the surface tension of PVA had to be determined. According to equation 2 of example 4, this can be determined when the pressure to cavitate is based solely on the case where the resistance to void growth is exclusively from the energy required to create surface area with no component from the resistance of elastic deformation. This situation occurs immediately after the solution is made. It is at this time that the sample is in its most liquid-like form. The surface tension was determined to be 0.04 N/m+/−#. This value of $\gamma$ can be used for all subsequent calculations of G for PVA gels at 10% polymer concentration.

Figure 1:
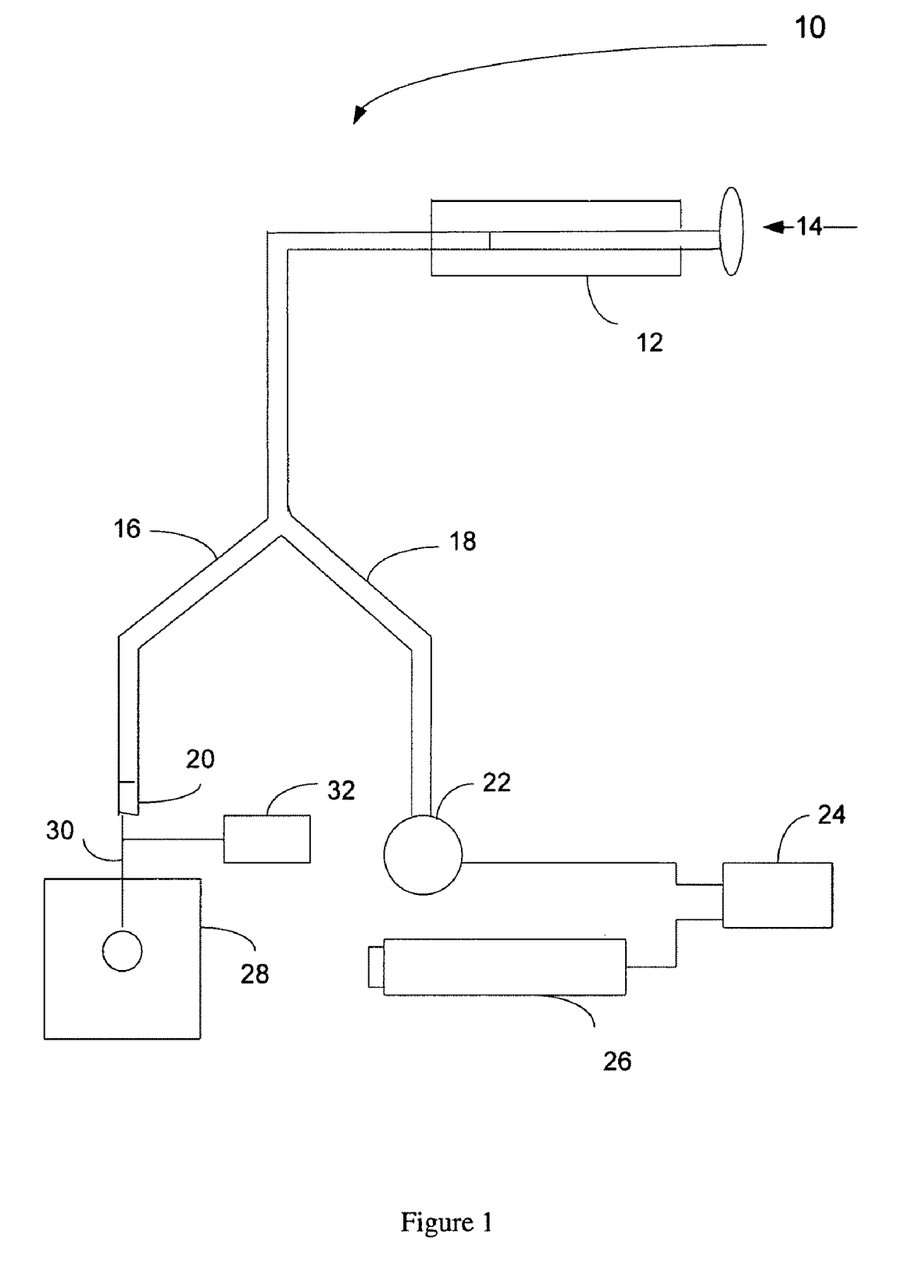
FIG. 1. Schematic diagram of an apparatus/system in accordance with certain embodiments of this invention.

Reference is made to FIG. 1 for a system and/or apparatus of the sort as can be used in conjunction with one or more methods of this invention. In particular, such an apparatus/system can be used to determine a mechanical modulus, as described herein. Apparatus 10 is shown with pump 12 in fluid connection with fluid source 14. Conduit components 16 and 18 direct fluid to terminal material contact component 20 and terminal pressure sensor component 22, respectively. Sensor component 22 is electronically connected or coupled to interface with monitor and/or computer component 24. Likewise, camera/video image component 26 is also electronically connected or coupled to interface with monitor/computer component 24. Fluid contact of terminal component 20 with material 28, through restricted flow portion 30, induces or forms a cavity therewithin. Components 22 and 24 monitor pressure within the cavity as a function of time, such data correlated with image(s) provided by camera 26. As further shown in FIG. 1, as applicable to certain non-limiting embodiments, pump 12 and restricted flow portion 30 can be provided as a syringe pump and a syringe needle, and such a needle can be coupled to actuator 32, all of which are commercially available from the referenced entities.

Figure 4:
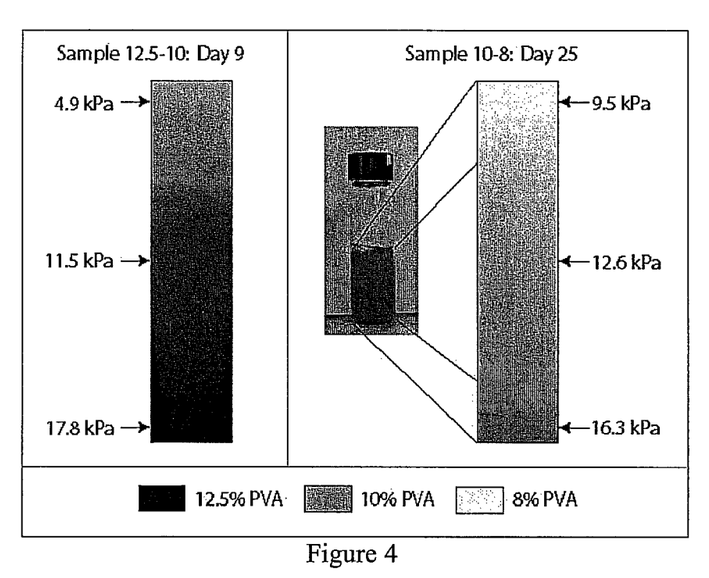
FIGS. 4-5. Cavitation along a PVA concentration gradient, showing change in modulus values therealong.

Experiments were then performed by cavitating the gel using syringe needles of different inner diameters along the same length scale of 101.6 um, 127 um, and 177.8 um. The results can be found in FIG. 4 (graph with ave value +/− in corner). The inner radius of the syringe needle was determined in this embodiment, non-limiting. This is intuitive as the force needed to cavitate a void normalized by the area of the initial void should result in a constant pressure needed to cavitate a void, thus proving measurement of a material property of the gel.

Figure 5:
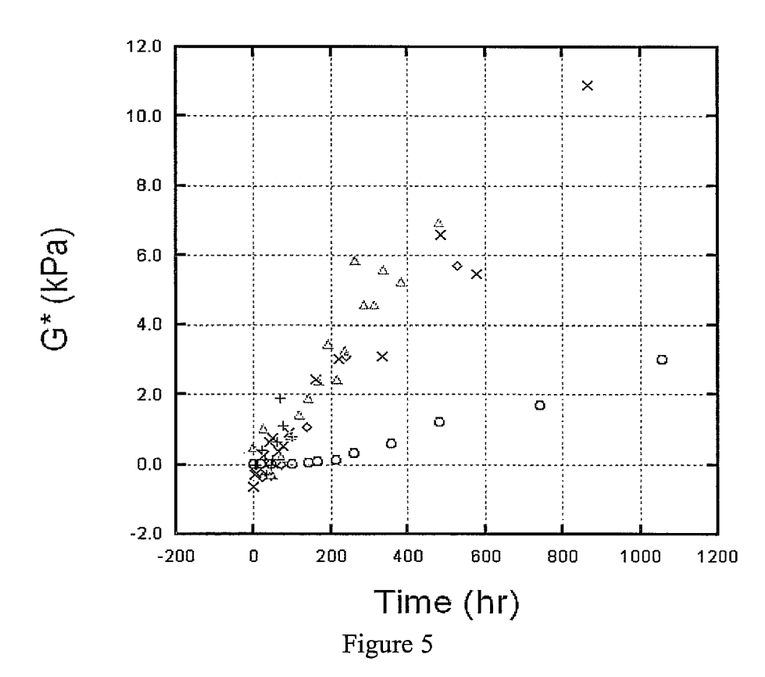

In order to show that this invention is sensitive enough to measure changes in the modulus of different gels, samples of a concentration gradient were made. (FIG. 5.) In these samples, a sample of PVA solution of a higher percent was put in a vial and then one of lower percent PVA was put on top of the initial solution. After a sufficient amount of days for the solutions to form a gel, a bubble growth measurement (BGM) was run at different heights within the samples and the resultant shear modulus values calculated. It is clear from the schematic that the modulus values decrease as the gradient goes from high PVA concentration down to a lower concentration. The modulus values for the 10% PVA after both 9 and 25 days can be compared to FIG. 5 where the modulus values of a gel were tracked with time. This experiment demonstrates that the BGM is capable of measuring modulus values local to the syringe tip.

The apparent modulus value of the PVA was then measured with time. From FIG. 5, it is apparent that the shear modulus, as expected, increases with time and that the values for G are within a factor of 5 from those obtained with classical rheological experiments.

The samples run in FIG. 5 had modulus values taken over time of samples that were left open to the atmosphere thus explaining the higher slope value as compared to that of rheology. The values obtained by BGM have a higher rate of sample hardening due to an increased loss of solvent. The sample taken by BGM in an area of controlled humidity shows a slope that is more similar to that taken by rheology as the syneresis was slowed.

Figure 6:
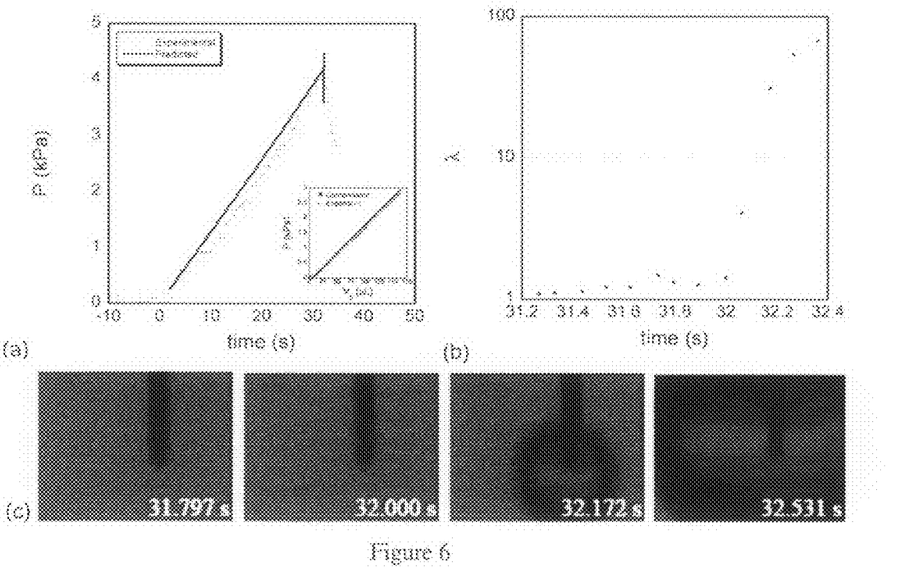
FIGS. 6A-C. A cavitation process as the pressure within a system increases with time. (A) Pressure in the system versus time both experimental and predicted. Inset shows pressure at tip of syringe versus compressed volume for cyclic loading at $P<P_c$ to demonstrate linearity of the system. (B) Extension ratio of the cavity with time. (C) Distal images of a cavitation event. The outer diameter of the syringe needle is 210 µm.

Cavitation in a hydrogel can be further considered with reference to triblock co-polymers of example 12. FIG. 6 illustrates a typical pressure history for a CRT experiment in a 15% PPP hydrogel system. At time t=0, the syringe pump begins compressing the volume of air, V, in the syringe system. V is defined by the balance:

$$V = V_o - \mu t + V_c \quad (4)$$

where $V_o$ is the volume of the system at t=0, $\mu$ is the pump compression rate, and $V_c$ is the volume of the cavity induced at the syringe needle tip. Assuming that air is immiscible with the hydrogel and the number of air molecules remains fixed, the pressure, P, as a function of time, t, can be described by:

$$\frac{P}{P_o} = \left(1 - \frac{\mu t}{V_o} + \frac{V_c(t)}{V_o}\right)^{-1} - 1 \quad (5)$$

where $P_o$ is the initial pressure in the system recorded for t<0. For $V_c/V_o \ll 1$, equation (5) predicts that P increases linearly with time, as observed in FIG. 6A. In fact, multiple cycles can be run for $P<P_c$ verifying the linearity of the measurement for an elastic material, as seen in the inset of FIG. 6A. At a critical pressure, $P_c$, the positive slope in the pressure history changes instantaneously. This change is related to the sudden dominant increase in the rate of cavity growth relative to $\mu$.

As seen in the images of FIG. 6C, the cavity at the syringe tip has very little growth until the critical pressure is reached. Within 200 ms, the cavity volume increases significantly. This sudden increase in the cavity size marks the onset of an elastic instability and is clearly observed in the sudden increase of the cavity extension ratio in FIG. 6B.

The introduction of a bubble, or cavity, into a Newtonian liquid follows the simple relationship of $P=2\gamma/r$, which relates the pressure, P, of the cavity to its size, r, and the surface energy, $\gamma$, of the liquid. For the growth of a cavity in an elastic network, the pressure is balanced by both the surface energy and elastic restoring energy of the surrounding material. The elastic restoring energy is conventionally described by the strain energy function, W, that relates the amount of elastic energy to the amount of strain imposed in a given material. For hydrogel materials, a simple strain energy function is the neo-Hookean relation:

$$w = (E/6)(2\lambda^2 + \lambda^{-4} - 3) \quad (6)$$

where E is an elastic coefficient that is equal to the linear modulus at small strains and $\lambda$ is the extension ratio of the cavity radius, $\lambda = r_c/r_{c_o}$. From this strain energy function, the pressure-growth relationship for a spherical void with internal pressure, P, can be determined. A. N. Gent and D. A. Tompkins, *Journal of Applied Physics* 1969, 40, 2520. A. N. Gent and C. Wang, *Journal of Materials Science* 1991, 26, 3392.

$$\frac{P_l}{E} = \frac{P - \frac{2\gamma}{r}}{E} = \frac{5}{6} - \frac{2}{3\lambda} - \frac{1}{6\lambda^4} \quad (7)$$

where $P_l$ is the elastic pressure contribution and $\lambda$ for our measurements is taken as the extension ratio of the cavity surface area $\lambda = (A_c/A_{c_o})^{1/2}$. Equation (7) is written for an incompressible material (i.e. Poisson's ratio=0.5), but equivalent expressions for general elastic materials are listed in many references. According to equation (7), the extension ratio approaches infinity as $P_l$ reaches a critical value of 5E/6 (FIG. 6).

Although cavity growth in equation (7) is monotonically dependent upon pressure, the conditions of the CRT experiments provide a clear definition of a critical pressure. Due to the conservation of air in the CRT experiment and controlled volume conditions for pressurization, the onset of "infinite" extension in the cavity causes a definitive change in the P vs. t curve. This behavior is described quantitatively by using equation (4) to determine $V_c$ and substituting into equation (5). Using an iterative numerical solution, this cavitation behavior can be predicted for the CRT experiment. As the model predicts, the critical, or maximum, pressure ($P_c$) is equal to 5E/6 for materials described by the neo-Hookean strain energy model (FIG. 6A). Therefore, the modulus of the elastic network can be determined as $E=6P_c/5$. This critical pressure is only sensitive to the volume of material roughly described by $r_s^3$ ($r_s$: inner radius of syringe); therefore, the CRT modulus measurement provides information on the local network structure. Note that the exact strain energy function for a given material may alter the exact value of the proportionality constant between E and $P_c$, but this constant ranges in general between 0.5 and 2.0. See, Y. Y. Lin and C. Y. Hui, *International Journal of Fracture*, 126 (3): 205-221, 2004. Therefore, CRT provides sufficient accuracy combined with the advantages of ease, efficiency, and spatial resolution for use in the development of soft materials, such as tissue scaffolds. Although cavitation has been observed in materials with moduli as large as $10^6$ Pa, different deformation mechanisms such as yielding or fracture invariably occur prior to cavitation in more rigid materials.

To demonstrate this technique, elastic moduli were measured using the CRT for three PPP hydrogels of polymer mass fractions 10, 15, and 20 wt %, with comparison of these values to measurements from classical shear rheology. This mechanical heterogeneity is not detectable using macroscopic shear rheology techniques. Reference is made to example 12, below.

Analogous considerations can be used to describe a microcavity mechanism in SIS membranes. Direct dependence on modulus is expected. The critical radius at which the microcavity separates from the syringe needle can be monitored and with a direct measurement of the cavity radius is not necessary. With controlled inducement of a single cavity formation and monitoring its growth and stability, the critical pressure and deformation history can provide insight into the local mechanical properties of a crosslinked matrix, such as SIS, in a straightforward and potentially high-throughput manner. Additionally, since this approach does not directly depend upon visual tracking devices, as with microparticle analysis, the local mechanical properties of matrices with non-transparent optical properties can also be fully characterized. Based on the typical macroscopic moduli (0.1-10 kPa) and surface energies of collagen-based hydrogels, a micro-cavity can be generated between 100 and 500 nm or smaller.

EXAMPLES OF THE INVENTION

The following non-limiting examples and data illustrate various aspects and features relating to the apparatus and/or methods of the present invention, including the determination of a mechanical modulus on, along or throughout a material or substrate, as is available through use of an apparatus of the sort described herein. In comparison with the prior art, the present methods and apparatus provide results and data which are surprising, unexpected and contrary thereto. While the utility of this invention is illustrated through the use of an apparatus and method for determining a modulus, it will be understood by those skilled in the art that comparable results and various other mechanical moduli are obtainable with various other apparatus and methods effected therewith, as are commensurate with the scope of this invention.

A cavitation rheology technique (CRT) related to this invention involves quantifying the pressure dynamics of a growing bubble, or cavity, within a soft solid or fluid. Cavity introduction is controlled and monitored with a custom-built, semi-automated instrument that consists of a syringe pump (New Era Syringe Pump—NE1000), pressure sensor (Omega Engineering—PX26-001GV), syringe needle (Fisher Scientific—91033), microscope (Edmunds Optics), and personal computer to record the pressure and microscope images of cavity growth as a function of time. A schematic of an instrument is shown in FIG. 1. The combined cost of the syringe, the needle, the pressure sensor, and tubing is approximately $150 demonstrating the cost advantage of the technique. The pressure and image acquisition can be controlled as would be understood by those skilled in the art using commercially-available software modified for such an application. Here, control was afforded by a custom-written program within National Instruments LabView software.

Example 1

PVA powder MW 13000-23000, 99.9% hydrolysis was purchased from Sigma Aldrich. The PVA gel was prepared in a manner similar to Wang. Wang, H. H.; Shyr, T. W.; Hu, M. S. *Journal of Applied Polymer Science* 1999, 74, (13), 3046-3052. The polymer in a mixed solvent of dimethyl sulfoxide and water in a 40/60 ratio with two percent boric acid as a crosslinking agent at 90° C. until the polymer was fully dissolved. The solution (e.g., about 8-15 wt. % PVA) was then cooled to room temperature whereafter the solution forms a gel. Unless stated, hydrogels of 10% PVA were used for further demonstration. (Samples were stored in airtight containers to prevent solvent loss.)

Example 2

Cone and plate shear rheometry is used to measure the shear moduli of the PVA gels on macroscopic length scales. These experiments were conducted on a cone plate Rheometer with a 40 mm cone at a two degree angle. A stress sweep was done to determine the frequency at which the subsequent time test was to be run at to ensure that the entirety of the test was performed in the linear elastic region. The time sweep was run at room temperature for one hour.

Example 3

To determine the local modulus, a semi-automated instrument was designed, as an embodiment of an apparatus of the sort presented herein, to induce and monitor a volume of air into a gel sample via a syringe pump. (FIG. 1.) All experiments were performed at a syringe pump rate of 400 µl/min. The initial air stream as introduced by the syringe pump is divided into two paths: one to induce the cavity within the gel and one to enable pressure monitoring as a function of time. A camera records cavity formation within the transparent gel. The pressure and image acquisition are controlled by a custom-written program within LabView.

Example 4

Figure 2:
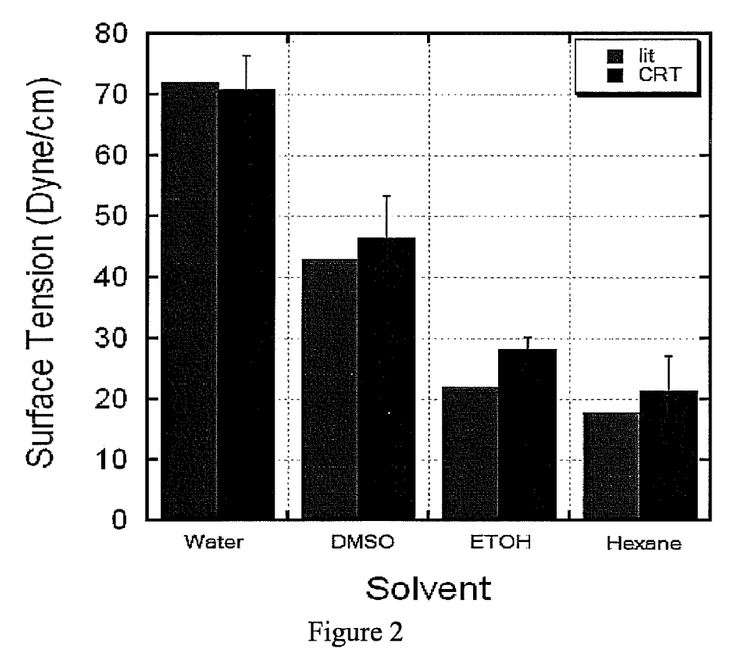
FIG. 2. Solvent surface tension measurements, for use in determination of shear modulus.

Calibration of the CRT setup was done by comparing the measured surface tension of different solvents to those values as found in the CRC. For a liquid, equation 2 is dependent only upon the second term as there is no contribution of bulk resistance. Therefore the $P_{cav}$ is equal to $2\gamma/r$. As seen in FIG. 2, there is good correlation between the values of $\gamma$ as measured by BGM to accepted values.

Example 5

The local mechanical properties of type 1 collagen gels have been measured to further demonstrate the utility of this invention. In these experiments, collagen gels were formed from Virtogen Type 1 collagen using a concentration of 2.3 mg/mL and adding 0.1 N NaOH to achieve a pH of 7.4. These matrices were gelled in chilled glass vials.

As described above, a syringe was used to penetrate a hydrogel matrix and subsequently pressurize the gas in the syringe needle to develop a gas micro-cavity, or bubble, within the hydrogel. During the pressurization process, the pressure history is recorded as a function of time, and the radial growth of the spherical cavity is monitored optically. From the pressure data, pressures increase as a function of time. At a critical pressure, the pressure drops as the bubble grows spontaneously until it detaches from the syringe needle. This growth and detachment process is also visually observed in the images. As discussed above, this point of cavity stability in a hydrogel can be correlated to the local modulus of the material. A measured critical pressure, gave a modulus of 490 Pa., such a pressure is slightly greater than the moduli reported in the scientific literature, but a non-optimized experimental instrument setup can easily explain this discrepancy.

The results show there is a significant increase in the pressure to generate a micro-cavity in the collagen gel compared to generating a cavity in water. Also, after an initial micro-cavity is formed in the collagen gel, subsequent micro-cavities only require a pressure equivalent to the cavitation pressure of water. This observation can be interpreted as the initial cavity locally fractures the collagen gel at the point of stability, and subsequent cavities are only grown in the water matrix of the collagen gel. Due to the maintenance of gel structure in the neighboring regions, the micro-cavities continue to be trapped in the gel surrounding the syringe needle. This initial data demonstrates measurement capability and its use for making straightforward, high-throughput measurements of local gel properties.

Example 6

The local and macroscopic mechanical properties of SIS are quantified using a combination of traditional experimental techniques and the present methods. To gain an understanding of the macroscopic mechanical properties of SIS, prepared membranes are tested under uniaxial tensile conditions. Although uniaxial measurements do not fully simulate the complex stress environment experienced in vivo, they do provide important insight into the general stiffness, strength, and reproducibility of the received membranes. An MTS Universal Testing machine is outfitted with an appropriate saline chamber to maintain hydration of the SIS sample during testing. Statistic sampling of the membranes and measurements for different membrane orientations are made. Additionally, macroscopic uniaxial measurements are conducted on every batch of specimens, to maintain consistency and statistical reproducibility in the sample library.

To properly understand the structure-property relationship for cavity growth in SIS, parallel experiments are conducted. The first path of experiments continue the preliminary results discussed earlier. These measurements explore the growth of cavities in prepared volumes of Type I collagen gels. The primary variables for these experiments are syringe diameter, pressure rate, and collagen concentration. These measurements allow further validation of the cavity growth technique under well-controlled conditions. Additionally, the optical properties of the collagen gel allow monitoring of the radial growth of the cavity. To complement the cavity growth experiments, a full array of structural characterization on the prepared collagen gels are also conducted. This structural characterization includes post-measurement SEM measurements of the collagen gel samples. This analysis helps connect the cavity growth mechanisms to specific changes in the collagen fiber network.

Example 7

In parallel to the measurements on controlled collagen gel, cavity growth experiments are conducted on prepared membranes of SIS. Similar to the measurements described above, the pressure history is quantified as a function of syringe diameter and pressure rate for SIS membranes. These two parameters provide insight into the critical length scale for micro- and macro-deformation processes in the SIS membranes. In addition the dependence of cavity growth mechanisms is investigated as a function of depth and lateral location. These measurements can provide insight into the mechanical heterogeneities associated with native SIS membranes. Accordingly, these local measurements are related to local structure information provided by microscopy on specimens before and after mechanical characterization.

Overall, these mechanical measurements can provide unique insight into the distribution of heterogeneous network structures within SIS membranes. Additionally, the methods of this invention, based on cavity growth, demonstrate a new technique that may have important applications in standardizing future tissue engineering applications. Current methods of local mechanical properties to assess uniformity and consistency in tissue scaffolds are complex and irreproducible. The cavity growth technique, can provide a quick, bench-top measurement (similar to a pH meter) that requires minimal analysis for general purposes. This capability, based on the demonstrated importance of mechanical properties for proper cell growth and tissue generation, will be important for the continued refinement and standardization of tissue engineering materials.

Example 8

Relating to an apparatus of this invention, micro-cavity growth experiments are performed on a custom-built instrument that is designed to optimally induce the growth of micro-cavities and monitor the pressure and growth histories simultaneously. This instrument is constructed around a sample platform on which a sample vial or dish is fixed. Above the sample platform, a syringe with a micro-tip needle is fixed to an Exfo Burleigh Inchworm actuator. The Inchworm actuator has a 50 mm displacement range to accommodate the full travel of the syringe. This displacement resolution of the actuator is sub-nanometer, and the velocity range is 4 nm/s to 2 mm/s. This range of parameter control is advantageous for investigating the rate-dependent properties of the local network structure in the SIS membranes, while also allowing a full-range of syringe needles to be used without encountering back-pressure effects due to unbalanced gas flows from the syringe. The Inchworm actuator, hence the syringe pressure and outflow, is controlled via personal computer with custom software written in the National Instruments Labview programming environment.

This custom program simultaneously records the pressure history and optical measurements. The pressure history is measured using a Sensotec pressure transducer that is connected to the syringe. The pressure accuracy is 6 Pa; therefore, significant insight can be gained into minute structural heterogeneities in the SIS network. The growth of the cavity, for transparent samples, is recorded using a CCD camera with variable-zoom lens that is fixed to the sample platform.

To assess the critical length scale for network structure-property relationships, a full range of syringe needles are used to induce micro-cavity growth. The inner diameter of the syringe needles is range from about 100 nm to about 400 microns. This full range of syringe needles is purchased form World Precision Instruments. The syringe needle dimension defines the diameter of the micro-cavity at the point of stability, thus defining the length scale of structural resistance to cavity growth.

Example 9

Cone and plate shear rheometry (TA Instruments Rheometer) was used to measure the hydrogel's shear moduli for comparison with the moduli values measured with CRT. A 2°, 40 mm acrylic cone was used for all samples. Stress controlled frequency sweeps (0.1-2.0 Pa depending on the sample) were performed in a range of 0.01-100 Hz. Although not rigorously true for all hydrogels, the materials were assumed to be isotropic and incompressible. This assumption is used to transform shear moduli data to linear elastic moduli for comparison the CRT data.

Example 10

With reference to examples 11-14, tests were performed at a syringe pump rate of 6.7 μL/s. The test begins with the controlled lowering of the syringe needle into the sample. An initial pressure signal is recorded. The air in the syringe is compressed via the syringe pump beginning at time, t, arbitrarily defined as t=0. The pressure within the system is measured throughout the experiment. Although images of the growing cavity are not necessary to determine the modulus for most materials, images are collected and can provide further insight into material properties.

Example 11

Linear triblock copolymers of PLA-PEO-PLA (PPP) were synthesized as previously described in literature but using solution polymerization (refluxing in toluene) instead of bulk polymerization. Using this technique, the chain lengths are controlled and the PDI is generally less than 1.1. For the experiments discussed here, the molecular weight of the PEO mid-block was 8800 g/mol and the end block molecular weights were 2700 g/mol for a total chain molecular weight of approximately 14,200 g/mol. Gels were prepared by slow addition of the dried polymer to DI water followed by stirring and heating. Crystallinity was inhibited in the end block domains by using poly(DL-lactide).

Example 12

Figure 7:
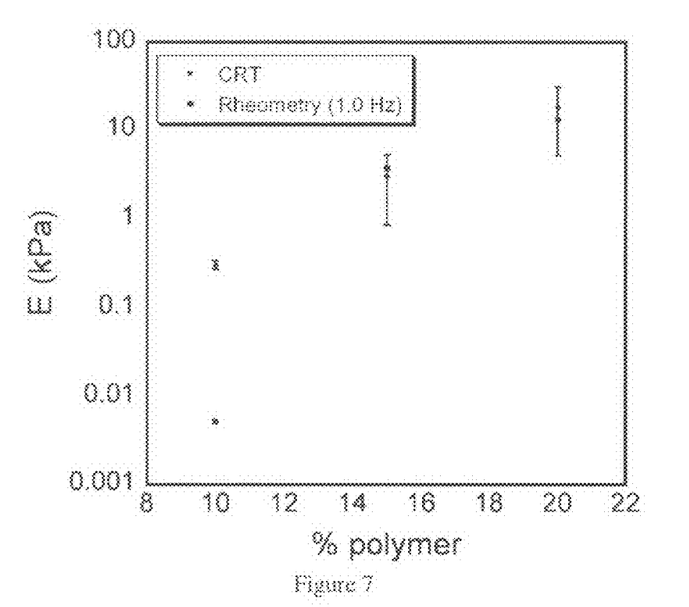
FIG. 7. Modulus versus percent polymer (PPP) in sample as determined by both CRT and classical rheology. $\gamma$ for these calculations was found to be 0.067 N/m.

The CRT method of this invention was compared with shear rheology using the PPP systems of example 11. FIG. 7 shows that the modulus increases with polymer concentration. This trend is expected due to the increase in crosslink density as the number of polymer chains per unit volume increases. More importantly, the modulus values from the CRT are similar compared to the values measured by classical cone and plate rheology. This observation verifies that the critical pressure of instability is closely related to the elastic modulus of the hydrogel.

At lower polymer concentrations, the CRT measures a higher modulus value. This deviation is due to the convolution of the surface tension properties. According to equation 4, the material-defined length scale ($2\gamma/E$) must be smaller than the inner radius (r) of the syringe for the pressure-instability to be sensitive to the modulus of the network. When $2\gamma/Er$ approaches or exceeds a value of 1, then surface tension will dominate the resistance to cavity growth. For the 10% PPP hydrogel, the surface tension term is equal to 13.4 as compared to a value of 0.39 for the 15% hydrogel and 0.23 for the 20% hydrogel.

The exact value of the CRT moduli is dependent on the apparent heterogeneities of the network. These heterogeneities give rise to distributions of moduli, which are reflected in the error bars in FIG. 3. Each data point is an average of six to ten measurements taken at different points within the sample. At lower polymer concentrations, it can be seen that the standard deviation of the measurements is small compared to samples of higher concentration. In fact, for the 20% PPP sample, heterogeneities were visually observed as dense polymer conglomerates at elevated temperatures.

Example 13

Figure 8:
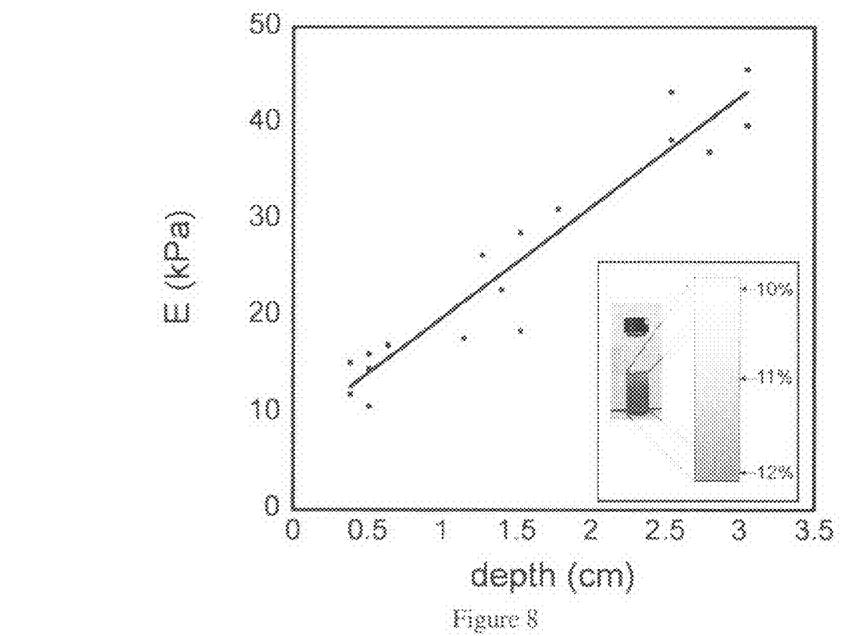
FIG. 8: Modulus as a function of depth for a concentration gradient sample in a PVA hydrogel. Inset shows the development of the gradient in the samples.

To emphasize a primary advantage of CRT to characterize heterogeneities throughout the bulk of a soft material, CRT was used to quantify the elastic modulus as a function of location in a PVA gradient hydrogel. The PVA gradient hydrogels were fabricated as shown in the FIG. 8 inset where 3 mL of a 12% PVA solution were put in a vial with a subsequent 3 mL of a 10% PVA solution put on top of the initial solution. With time, limited diffusion occurs across the two concentrations resulting in the formation of a natural gradient. Diffusion is arrested by the onset of the gel network. CRT measurements were then taken at different heights within the samples. It is clear from the graph in FIG. 8 that the modulus values increase as the gradient goes from lower to higher PVA concentration. Related to the same mechanism observed in the PPP hydrogel data in FIG. 7, this increase in modulus with increasing polymer concentration arises from an increase in crosslink density within the system.

Example 14

Figure 9:
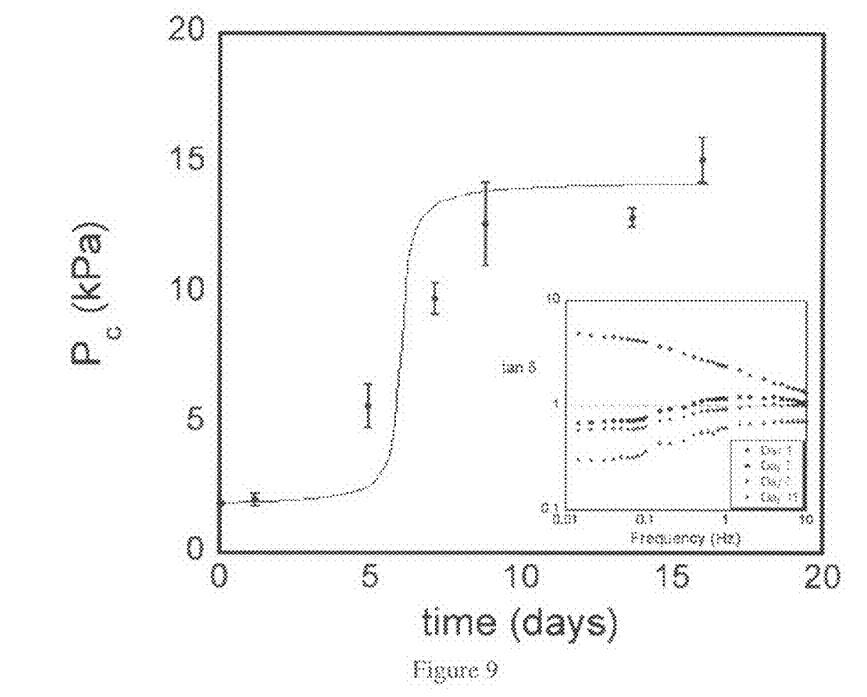
FIG. 9: Gelation time of PVA hydrogel determined by CRT compared with shear rheometry (frequency of 1.5 Hz) where the liquid-like to solid-like transition can be observed at tan $\delta=1$. The inflection point of the increase in $P_c$ reflects the gel transition in the CRT experiments. The solid line through the CRT data is for illustrative purposes.

CRT can also be used to quantify the dynamics associated with gelation, or the onset of the hydrogel network. To demonstrate this, we measure the critical pressure of cavitation was measured as a function of process time, $t_p$, in PVA hydrogels. The time $t_p=0$ is defined as the time at which the polymer solution is made. Therefore, at short times, the pressure associated with the cavity instability relates to the resistance provided by the surface energy of a viscous fluid. As time proceeds, the PVA molecules form semi-crystalline domains, which serve as physical crosslinks to form a polymer network. As $t \rightarrow \infty$, the formation of semi-crystalline regions will be balanced by the osmotic stresses of the water content and the elasticity of the chains between physical crosslinks; therefore, the critical pressure will plateau. This transition of $P_c$ is shown in FIG. 9. Although the exact relationship between $P_c$ and the relevant material properties for a viscoelastic fluid (e.g. $\eta'$, $\eta''$, or G', G") are not currently known, the inflection point observed in FIG. 9 can be assumed to be approximately equal to the onset of a gel network. This assumption is verified through shear rheometry measurements of PVA hydrogels as a function of time after mixing (FIG. 9). Accordingly, the transition in tan δ can be used to track the change from liquid-like to solid-like behavior of a material. This transition is observed when tan δ is equal to 1 over all frequencies. This transition in tan 6 curves was seen between 5 and 6 days confirming that found with CRT.

Example 15

Similar to data for the PPP hydrogel, the final moduli values of the PVA hydrogel are similar for both CRT and shear rheometry. The modulus measured from bulk rheology after 260 hours was approximately 2 kPa compared to a modulus of 5 kPa determined by the CRT. As discussed above, this discrepancy is most likely associated with differences in the exact nature of the strain energy function. In fact, based on the PVA gelation process, it may be that many uncrosslinked polymer chains still exist, thus causing an unknown viscoelastic contribution to $P_c$.

As demonstrated above, development of tissue scaffolds and the characterization of naturally heterogeneous biological tissues can be facilitated by determination of the local modulus at an arbitrary point within a soft material. The methods, systems and apparatus of this invention can be illustrated by growing a cavity at the tip of a syringe needle and monitoring the pressure of the cavity at the onset of a mechanical instability. This critical pressure can be directly related to the local modulus of the material. While results and data are provided for the network development of poly(lactide)-poly(ethylene oxide)-poly(lactide) triblock copolymer and poly(vinyl alcohol) hydrogels, such materials can serve as model materials for tissue scaffolds and soft biological tissues. Accordingly, this invention not only provides an easy, efficient, and economical method to guide the design and characterization of soft materials, but it also provides quantitative data of the local mechanical properties in naturally heterogeneous materials.

We claim:
1. A method of determining a mechanical modulus of a non-liquid material, said method comprising:

providing a non-liquid material;

introducing a fluid into said material for at least one of a time and a pressure at least partially sufficient to induce a void within said material;

moderating the pressure within the void; and determining a mechanical modulus of said material by measuring the maximum pressure within said void upon void instability, said maximum pressure directly related to said mechanical modulus of said material.

2. The method of claim 1 wherein said material is selected from a biological tissue and a biomimetic material.

3. The method of claim 1 wherein a plurality of voids are induced within said material to determine said modulus at a plurality of material locals.

4. The method of claim 3 wherein said material comprises at least one of a structural heterogeneity and a compositional heterogeneity.

5. The method of claim 4 wherein said modulus is determined on a length scale from about 10 μm to about 50 μm.

6. The method of claim 1 determining an elastic modulus of said material.

7. The method of claim 6 wherein said void pressure indicates the elastic modulus of said material at the local of said material.

8. The method of claim 7 wherein said determination comprises video monitoring of said void correlated to at least one of said fluid introduction and pressure monitoring.

9. The method of claim 1 wherein said determination is compared to a microscopic structural analysis of said material.

10. The method of claim 1 comprising a plurality of materials and modulus determinations.

11. A method of using cavitation to determine a local elastic modulus of a material, said method comprising:

providing a non-liquid material;

introducing a fluid selected from at least one of a gas and air into said material at a local therein, for at least one of a time and a pressure at least partially sufficient to induce a cavity within said material;

monitoring cavity pressure; and determining the elastic modulus of said material at said local through the relationship $E=(6/5)(P_c-2\gamma/r)$, where $E$ is Young's elastic modulus, $\gamma$ is the surface tension between said fluid and said non-liquid material, $r$ is the initial radius of said cavity set by the dimension of a needle introducing said fluid and $P_c$ is the maximum pressure at onset of cavity instability.

12. The method of claim 11 wherein said material is selected from a biological tissue and a biomimetic material.

13. The method of claim 12 wherein a plurality of cavities are induced within said material, to determine said elastic modulus at a plurality of material locals.

14. The method of claim 13 wherein said material comprises at least one of a structural heterogeneity and a compositional heterogeneity.

15. The method of claim 14 wherein said material comprises a biological tissue comprising layered components.

16. The method of claim 14 wherein said elastic modulus is determined on a length scale of a biological cell.

17. The method of claim 11 wherein said determination comprises video monitoring of said cavity correlated with at least one of fluid introduction and pressure monitoring.

18. The method of claim 11 wherein said determination is compared to a microscopic structural analysis of said material.

19. A system for measurement of a mechanical modulus, said system comprising:

a non-liquid material comprising a mechanical modulus, said material selected from a biological tissue and a biomimetic material; and a fluid source in fluid communication with a material contact component and a pressure sensor component, said contact component comprising a restricted flow portion.

20. The system of claim 19 wherein said restricted flow portion comprises a syringe needle, and said source comprises a syringe pump.

21. The system of claim 19 comprising a monitor component interfaced with said sensor component.

22. The system of claim 21 wherein said monitor comprises a computer component.

23. The system of claim 22 comprising a video image component interfaced with said computer component.

24. The system of claim 19 wherein said material comprises at least one of a structural heterogeneity and a compositional heterogeneity.

25. The system of claim 23 wherein said contact component is positionable within said material at a length scale of about 10 μm to about 50 μm.

26. The system of claim 25 wherein said system comprises an actuator component.

* * * * *